(12) United States Patent
Adams

(10) Patent No.: US 8,663,274 B2
(45) Date of Patent: Mar. 4, 2014

(54) IMPLANTABLE TISSUE FASTENER AND SYSTEM FOR TREATING A GASTROINTESTINAL TRACT

(75) Inventor: Ronald Adams, Holliston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 22 days.

(21) Appl. No.: 13/419,635

(22) Filed: Mar. 14, 2012

(65) Prior Publication Data

US 2012/0172899 A1    Jul. 5, 2012

Related U.S. Application Data

(60) Continuation of application No. 10/705,127, filed on Nov. 12, 2003, now Pat. No. 8,157,836, which is a continuation of application No. 10/200,337, filed on Jul. 23, 2002, now Pat. No. 6,669,713, which is a continuation of application No. 09/551,754, filed on Apr. 18, 2000, now Pat. No. 6,447,533, which is a division of application No. 09/084,001, filed on May 26, 1998, now Pat. No. 6,113,609.

(51) Int. Cl.
    *A61B 17/08* (2006.01)

(52) U.S. Cl.
    USPC ............ 606/213; 606/153; 606/214; 606/217

(58) Field of Classification Search
    USPC .......................................... 606/153, 213–219
    See application file for complete search history.

(56) References Cited

U.S. PATENT DOCUMENTS

| | | | |
|---|---|---|---|
| 3,874,388 A | 4/1975 | King et al. | |
| 5,088,979 A | 2/1992 | Filipi et al. | |
| 5,141,516 A | 8/1992 | Detweiler | |
| 5,331,975 A | 7/1994 | Bonnuti | |
| 5,350,399 A | 9/1994 | Erlebacher et al. | |
| 5,403,326 A | 4/1995 | Harrison et al. | |
| 5,411,508 A | 5/1995 | Bessler et al. | |
| 5,413,571 A | 5/1995 | Katsaros et al. | |
| 5,460,610 A | 10/1995 | Don Michael | |

(Continued)

FOREIGN PATENT DOCUMENTS

| | | |
|---|---|---|
| EP | 0 474 887 | 3/1992 |
| FR | 2 714 284 | 6/1995 |
| WO | WO 97/41779 | 11/1997 |

OTHER PUBLICATIONS

Mason, Rodney J., et al., "A New Intraluminal Antigastroesophageal Reflux Procedure in Baboons," Gastrointestinal Endoscopy, (1997), 45(3):283-290.

(Continued)

*Primary Examiner* — Julian W Woo
(74) *Attorney, Agent, or Firm* — Bookoff McAndrews, PLLC

(57) ABSTRACT

A system including an implantable fastener for fastening layers of tissue is disclosed. In one embodiment, the fastener includes a proximal anchor member and a distal anchor member each being movable from a reduced profile position to a deployed position. The anchor members are mesh structures capable of moving to the deployed position by reducing the axial spacing between opposite ends of the anchor members. Methods of treating gastroesophageal reflux disease (GERD) are also disclosed. One of the methods includes placing the distal anchor member through a hole formed in the wall of the esophagus and through a hole formed in the gastric wall. The distal anchor member and the proximal anchor member are then placed in their deployed positions to fasten the wall of the esophagus and the gastric wall together between the anchor members.

13 Claims, 9 Drawing Sheets

(56) References Cited

U.S. PATENT DOCUMENTS

| | | |
|---|---|---|
| 5,571,116 A | 11/1996 | Bolanos et al. |
| 5,573,169 A | 11/1996 | Green et al. |
| 5,582,616 A | 12/1996 | Bolduc et al. |
| 5,588,965 A | 12/1996 | Burton et al. |
| 5,649,959 A | 7/1997 | Hannam et al. |
| 5,676,674 A | 10/1997 | Bolanos et al. |
| 5,690,674 A | 11/1997 | Diaz |
| 5,769,870 A | 6/1998 | Salahieh et al. |
| 5,853,422 A | 12/1998 | Huebsch et al. |
| 5,888,196 A | 3/1999 | Bonnuti |
| 6,447,533 B1 | 9/2002 | Adams |

OTHER PUBLICATIONS

Obora, Yoshiro et al., Neurol. Med. Chir., Tokyo (1980), 20:497-505.

IMPLANTABLE TISSUE FASTENER AND SYSTEM FOR TREATING A GASTROINTESTINAL TRACT

This is a continuation of application Ser. No. 10/705,127, filed Nov. 12, 2003, now U.S. Pat. No. 8,157,836, which is a continuation of Ser. No. 10/200,337 filed on Jul. 23, 2002, now U.S. Pat. No. 6,669,713, which is a continuation of Ser. No. 09/551,754, filed Apr. 18, 2000, now U.S. Pat. No. 6,447,533, which is a divisional of 09/084,001, filed May 26, 1998, now U.S. Pat. No. 6,113,609, which are incorporated herein by reference.

BACKGROUND OF THE INVENTION

1. Field of the Invention

The present invention relates to an implantable tissue fastener for fastening layers of tissue together. More particularly, the present invention relates to a system and method for fastening of the wall of the esophagus and the gastric wall together to treat gastroesophageal reflux disease (GERD).

2. Description of Related Art

The lower esophageal sphincter is located in a distal portion of the esophagus adjacent to the junction between the esophagus and the stomach. When food is digested, a properly functioning lower esophageal sphincter allows food to pass from the esophagus to the stomach while limiting reverse flow of the stomach contents into the esophagus.

Gastroesophageal reflux disease (GERD) is a disorder in which the lower esophageal sphincter allows contents of the stomach including gastric acid and bile to reverse flow into the distal portion of the esophagus during digestion. Complications associated with GERD include heartburn, pulmonary disorders, chest pain, esophageal ulcers, esophagitis, Barrett's esophagus, and esophageal carcinoma.

A common treatment for GERD includes administering prescription acid blockers for limiting gastric production of acid. Although these drugs may provide short term relief, the drugs merely alleviate some of the symptoms of GERD rather than correcting the underlying dysfunction of the lower esophageal sphincter. In addition, acid blockers are expensive, and any long term complications associated with using acid blockers are unknown.

Various surgical procedures have been attempted to correct GERD. In one surgical procedure, known as Nissen fundoplication, a portion of the gastric fundus is wrapped around the esophagus. The wrapped gastric fundus applies pressure to the esophagus to limit reverse flow of the stomach contents into the esophagus. Conventional fundoplication procedures are effective at treating GERD, but they have a number of disadvantages. Open procedures require a large incision to expose the stomach and the lower esophagus. In laparoscopic procedures, four or five smaller incisions are formed in the abdominal wall to insert instruments into the body of the patient. However, such procedures are expensive and sometimes require a significant amount of time for patient recovery.

Some other procedures, such as those disclosed in U.S. Pat. No. 5,403,326 and in U.S. Pat. No. 5,571,116, use surgical staples to secure the fundus of the stomach and the lower esophagus. However, these staples have relatively small cross sectional sizes which concentrate stresses and could allow for tearing or cutting of tissue. In addition, some of the relatively rigid stapling instruments used in these procedures may damage tissue when they are moved in a patient. Also, such rigid instruments are inserted into the operative field with trocar type devices which make abdominal wall penetrations. These abdominal wall penetrations increase the risks of post-operative hernias, accidental organ perforations, or other drawbacks associated with laparoscopic surgery.

In light of the foregoing, there is a need in the art for an improved fastener and procedure for treating GERD.

SUMMARY OF THE INVENTION

Accordingly, the present invention is directed to a fastener, system, and method that substantially obviate one or more of the limitations of the related art. To achieve these and other advantages and in accordance with the purpose of the invention, as embodied and broadly described herein, the invention includes an implantable fastener for fastening layers of tissue together. The fastener includes an elongated support and a distal anchor member having a first end portion connected to the support and a second end portion movable on the support. The distal anchor member is configured to be movable from a reduced profile position to a deployed position when a spacing between the first and second end portions is reduced. The fastener also includes a proximal anchor member having first and second end portions movable on the support. The proximal anchor member is configured to be movable from a reduced profile position to a deployed position when a spacing between the first and second end portions of the proximal anchor member is reduced, and the proximal anchor member is spaced from the distal anchor member a distance sufficient to position the layers of tissue together between the proximal and distal anchor members. At least one retainer is provided on a proximal end portion of the support. The retainer engages one of the end portions of the proximal anchor member when at least the proximal anchor member is in the deployed position.

In another aspect, the fastener includes a first anchor member, a second anchor member, and a connecting section connecting the proximal end portion of the first anchor member to the distal end portion of the second anchor member. An elongated support is connected to the distal end portion of the first anchor member. The support is movable proximally in the second end portion of the distal anchor member, in the connecting section, and in the second anchor member to place the first and second anchor members in the deployed positions.

In another aspect, the fastener includes an inflatable balloon and a cap member.

In a further aspect, a system for fastening tissue is provided. The system includes the fastener and structure for inserting and/or deploying the fastener.

In yet another aspect, the present invention includes a method of treating gastroesophageal reflux disease. In the method, the implantable fastener is passed transorally through the esophagus to a position near the junction between the esophagus and the stomach. The distal anchor member is inserted through a hole formed in the wall of the esophagus and through a hole formed in the gastric wall while the distal anchor member is in the reduced profile position. Both the distal anchor member and the proximal anchor member are placed in the deployed positions to fasten the wall of the esophagus and the gastric wall together between the deployed distal anchor member and the deployed proximal anchor member.

In a further aspect, the method according to the invention includes inflating a balloon in the stomach and placing a cap member against the esophageal wall.

In another aspect, the invention includes a method of fastening at least two layers of tissue together. This method comprises introducing an adhesion inducing agent between first and second tissue layers of a body, inserting an implantable fastener in the body, and holding the first and second tissue layers together with the implantable fastener while the adhesion inducing agent is between the first and second tissue layers.

It is to be understood that both the foregoing general description and the following detailed description are exemplary, and are intended to provide further explanation of invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
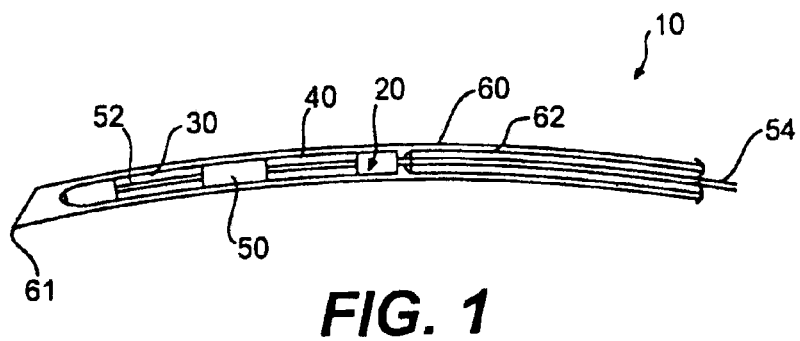
FIG. 1 is view of a distal end portion of a tissue fastening system according to a first embodiment of the invention.

Reference will now be made in detail to the present preferred embodiments of the invention, examples of which are illustrated in the accompanying drawings. Wherever possible, the same reference numbers are used in the drawings and the description to refer to the same or like parts, and similar reference numerals are used to refer to similar elements.

FIGS. 1-7 show a tissue fastening system 10 according to a first embodiment of the invention. As shown in FIGS. 1, 3, and 5-7, the system 10 includes an implantable fastener 20 having a distal anchor member 30, a proximal anchor member 40, and a connecting section 50 connecting a proximal end portion of the distal anchor member 30 to a distal end portion of the proximal anchor member 40.

Figure 3:
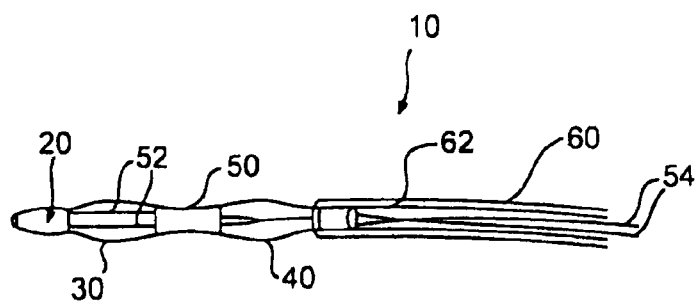
FIG. 3 is a view similar to FIG. 1 showing a tissue fastener of the system extending from an introducer tube.
Figure 6:
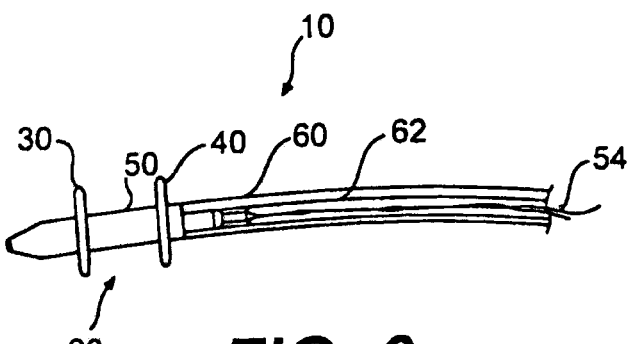
FIG. 6 is view similar to FIG. 3 showing deployment of anchor members on the fastener.
Figure 7:
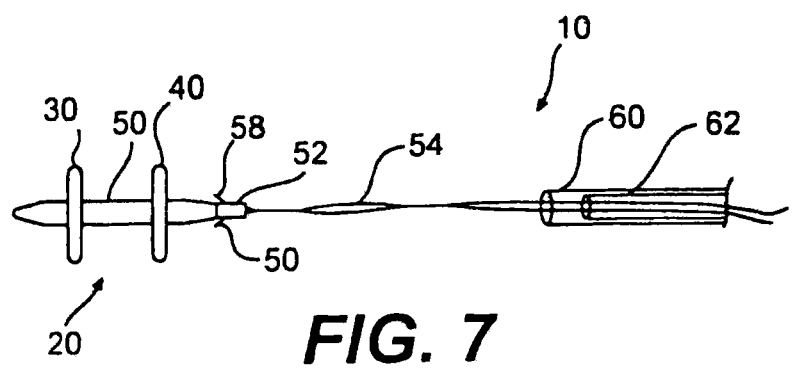
FIG. 7 is a view similar to FIG. 6 showing the introducer and pusher tube being withdrawn from the fastener after the anchor members are deployed.

The distal anchor member 30 is constructed to be moved from a reduced profile position, shown in FIGS. 1 and 3, to a deployed (expanded) position, shown in FIGS. 6 and 7. The proximal anchor member 40 is preferably constructed similar or identical to the distal anchor member 30. The proximal anchor member 40 is also movable from a reduced profiled position shown in FIGS. 1 and 3, to a deployed (expanded) position, shown in FIGS. 6 and 7.

Preferably, the distal anchor member 30 and proximal anchor member 40 are constructed to move from their respective reduced profile positions to their respective deployed positions in response to axial compressive forces reducing the axial spacing between opposite end portions of the anchor members 30 and 40. In other words, the distal anchor member 30 is preferably constructed so that it expands to the deployed position when a spacing between proximal and distal end portions of the distal anchor member 30 is reduced. Similarly, the proximal anchor member 40 is preferably constructed so that it expands to the deployed position when a spacing between proximal and distal end portions of the proximal anchor member 40 is reduced.

The distal and proximal anchor members 30 and 40 are preferably mesh structures including individual filaments braided or woven together. Preferably, the anchor members 30 and 40 are made of expandable, woven mesh material. For example, the anchor members 30 and 40 are mesh structures having filaments formed at least in part of nylon material. In the relaxed, reduced profile position shown in FIGS. 1 and 3, the distal and proximal anchor members 30 and 40 have a generally cylindrical shape. In the expanded, deployed position, shown in FIGS. 6 and 7, the distal and proximal anchor members 30 and 40 have a generally annular disk shape.

Figure 8:
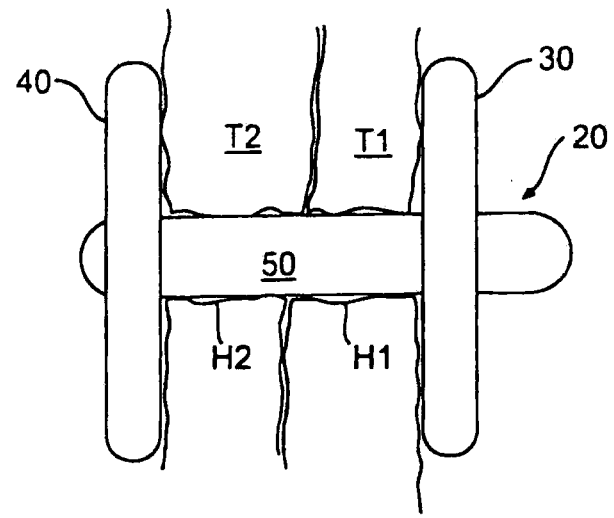
FIG. 8 is a schematic view showing how the fastener of the system of FIGS. 1-7 fastens layers of body tissue when the anchor members are deployed.

FIG. 8 shows how the fastener 20 fastens tissue. The distal end of the fastener 20 is inserted in holes H1 and H2 formed in tissues layers T1 and T2, respectively, while the distal anchor member 30 is in the reduced profile position. Preferably, the connecting section 50 has a length sufficient to pass through both tissue layers T1 and T2. The distal anchor member 30 is deployed and placed against a surface of one of the tissue layers T1, and the proximal anchor member 40 is deployed and placed against the surface of the other tissue layer T2. This fastens the tissue layers T1 and T2 together between the deployed anchor members 30 and 40.

In an alternative construction of the fastener 20, a single piece of mesh material forms both of the anchor members 30 and 40 and a layer of material coated on the mesh material between the anchor members 30 and 40 forms the connecting section 50.

Figure 5:
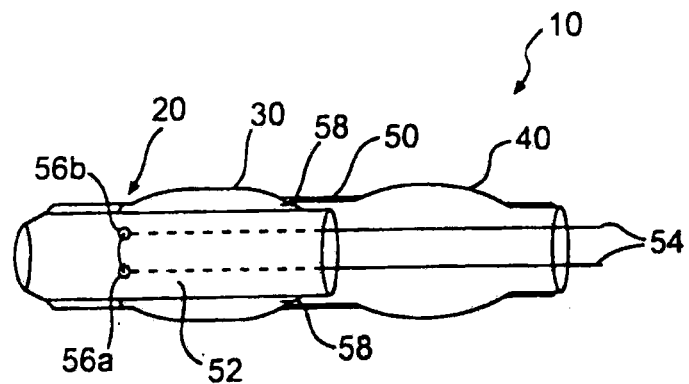
FIG. 5 is a schematic view showing the fastener and portion of an actuator of the system of FIG. 1.

As shown in FIG. 5, a distal end portion of the distal anchor member 30 is connected to an outer surface of an elongated, tubular shaped, support member 52. The tubular support member 52 has an outer diameter smaller than the inner diameter of the proximal anchor member 40, the inner diameter of the connecting section 50, and the inner diameter of the portion of the distal anchor member 30 that lacks connection to the support member 52.

An actuator 54 is removably coupled to the support member 52 as shown in FIG. 5. The actuator 54 passes through a lumen of the support member 52 and through a proximal end portion of fastener 20. The actuator 54 preferably includes a length of thread material (or wire) passing through a pair holes 56a and 56b in the support member 54 so that a portion of the thread is positioned on an outer surface of the support member 52. Because the thread passes through the holes 56a and 56b, the thread is capable of being removed from the support member 52 and fastener 20 by pulling one end of the thread.

Proximal movement of the actuator 54 moves the support member 52 proximally in the distal anchor member 30, in the connecting section 50, and in the proximal anchor member 40 when a distally directed pushing force is applied at a proximal end of the fastener 20. Because the distal end of the support member 52 is connected to the distal end of the distal anchor member 30, the proximal movement of the support member 52 moves the distal end of the fastener 20 toward the proximal end of the fastener 20. Initially, the proximal movement of the support member 52 reduces the spacing between the opposite ends of the distal anchor member 30 and further proximal movement of the support member 52 eventually places the distal anchor member 30 in the deployed position. After the distal anchor 30 moves to the deployed position, the continued proximal movement of the support member 52 reduces the spacing between opposite ends of the proximal anchor member 40 to place the proximal anchor member 40 also in the deployed position.

As shown in FIG. 5, a proximal end portion of the support member 52 includes one or more retainers 58. Preferably, the retainers 58 are configured to engage a proximal end portion of the proximal anchor member 40, as shown in FIG. 7, so that the distal and proximal anchor members 30 and 40 are retained in their deployed positions. In the embodiment shown in FIGS. 5 and 7, the retainers 58 are flaps of resilient material extending from the outer surface of the support member 52 so that the retainers 58 engage a proximal end of the fastener 20 after the support member 52 moves a sufficient distance out of an opening in the proximal end of the fastener 20. Alternatively, the retainers 58 could be other types of engagement mechanisms, such as locking ribs or teeth.

The system 10 also includes structure for inserting the fastener 20 and for deploying the anchor members 30 and 40. As shown in FIGS. 1-4, 6, and 7, the system 10 includes a relatively flexible introducer tube 60 and a relatively flexible pushing member 62 extending in the introducer tube 60. A distal end portion of the introducer tube 60 has an inner diameter sized to contain the fastener 20 therein, as shown in FIG. 1. The distal end of the introducer tube 60 has a sharp needle tip 61 capable of puncturing the esophageal and gastric walls. A proximal end portion of the introducer tube 60, shown in FIGS. 2 and 4, has a first connector 64 configured to be connected with a corresponding second connector 66 on the pushing member 62. In addition, the proximal end portion of the introducer tube 60 has a gripping member 65 allowing a physician to retract the introducer tuber 60 in the proximal direction after the fastener 20 is within the gastric lumen.

Figure 2:
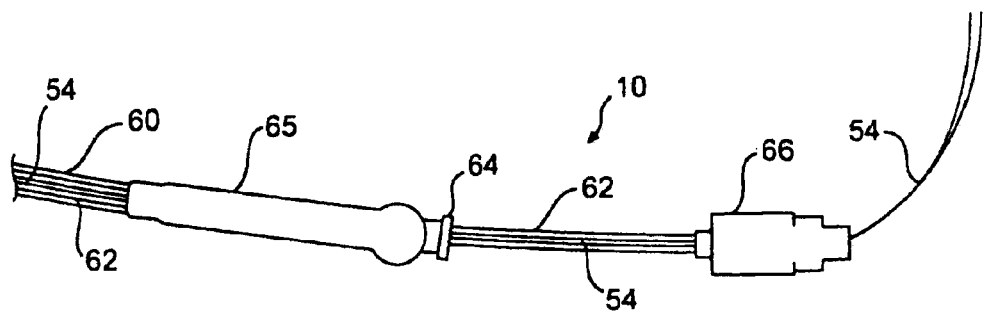
FIG. 2 is a view of a proximal end portion of the tissue fastening system of FIG. 1.

The pushing member 62 is a tube axially movable in the lumen of the introducer tube 60. When the fastener 20 is introduced into the body of a patient, the fastener 20 is positioned in the distal end portion of the introducer tube 60 and the pushing member 62 is in a retracted position, as shown in FIGS. 1 and 2, so that a distal end of the pushing member 62 is spaced from the distal end of the introducer tube 60.

Figure 4:
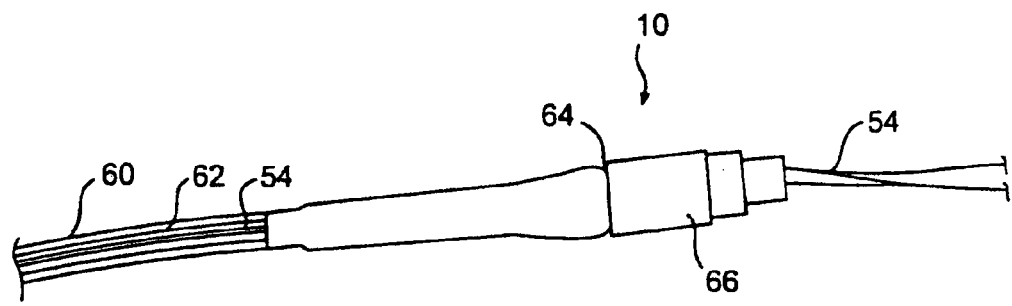
FIG. 4 is a view similar to FIG. 2 showing the connection of the introducer tube and pusher tube when the introducer extends from the introducer tube as shown in FIG. 3.

The distal end of the pushing member 62 has an opening with an inner diameter smaller than the outer diameter of the proximal end portion of the fastener 20. Distal movement of the pushing member 62 with respect to the introducer tube 60 pushes the distal and proximal anchor members 30 and 40 through the distal opening in the introducer tube 60, as shown in FIG. 3. When the pushing member 62 is in this position, the first connector 64 is capable of being connected to the second connector 66, as shown in FIG. 4.

The actuator 54 extends through a lumen in the pushing member 62 and passes through an opening in the second connector 66. After the first connector 64 is connected to the second connector 66, the actuator 54 is moved in the proximal direction. During proximal movement of the actuator 54, the distal end of pushing member 62 contacts the proximal end of the fastener 20 and applies a distally directed pushing force to limit proximal movement of the fastener 20 in the introducer tube 60. The initial proximal movement of the actuator 54 moves the support member 52 in the fastener 20 to place the distal anchor member 30 in the deployed position shown in FIG. 6. Continued proximal movement of the actuator 54 moves support member 52 further in the fastener 20 to place the proximal anchor member 40 in the deployed position shown in FIG. 6. Eventually, the retainers 58 engage the proximal end of the fastener 20, as shown in FIG. 7, and limit distal movement of the support member 52 in the fastener 20 to thereby retain the anchor members 30 and 40 in the deployed positions.

When the retainers 52 have engaged the proximal end of the fastener 20, the introducer tube 60 and pushing member 62 are pulled away from the fastener 20, as shown in FIG. 7. In addition, the actuator 54 is preferably uncoupled from the support member 52. For example, when the actuator 54 includes thread, one end of the thread is pulled to pass the other end of the thread through the holes 56a and 56b shown in FIG. 5.

Figure 9:
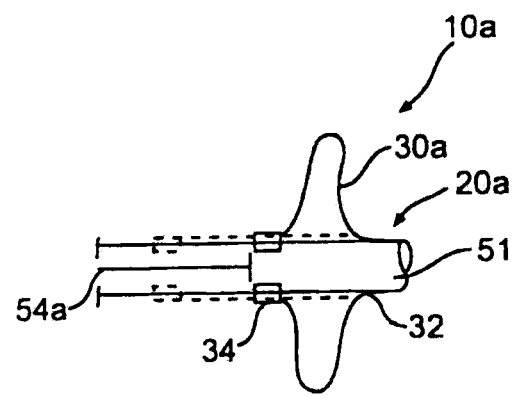
FIG. 9 is a schematic view of a distal end portion of a tissue fastening system according to a second embodiment of the invention.
Figure 10:
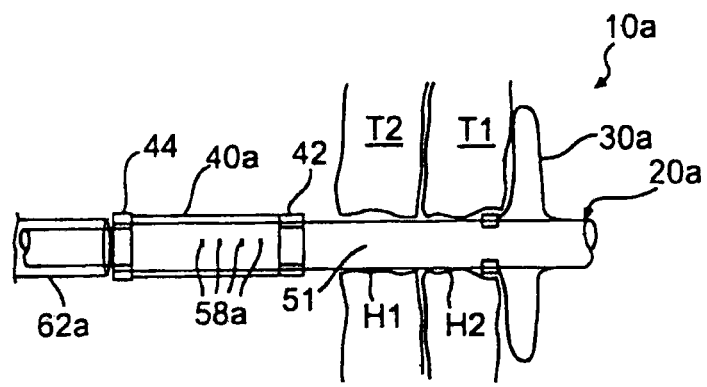
FIG. 10 is a schematic view of the system of FIG. 9 showing how a proximal anchor member is deployed after a distal anchor member is deployed.

FIGS. 9 and 10 show an alternative embodiment of a tissue fastening system 10a. As shown in FIG. 9, the tissue fastening system 10a includes a fastener 20a having a distal anchor member 30a including a distal end portion 32 connected to an elongated support member 51 and a proximal end portion 34 slidably mounted on the support member 51. An axially movable actuator 54a is provided in a lumen of the support member 51. The actuator 54a has a distal end configured to contact the slidable distal end portion 34 of the distal anchor member 30a.

The distal anchor member 30a preferably has a mesh structure similar to the distal anchor member 30 of the system 10 shown in FIGS. 1-7. The distal anchor member 30a is moved from a reduced profile position, illustrated with broken lines in FIG. 9, to a deployed position, shown in FIG. 9, when the actuator 54a is moved in the distal direction to slide the proximal end portion 34 toward the distal end portion 32.

When the distal anchor member 30a is deployed and the support member 51 passes through holes H1 and H2 formed in tissue layers T1 and T2, as shown in FIG. 10, positioning the distal anchor member 30a against the tissue layer T1 maintains the distal anchor member 30a in the deployed position.

As shown in FIG. 10, the system 10a also includes a proximal anchor member 40a preferably having a mesh structure similar to the proximal anchor member 40 of the system 10 shown in FIGS. 1-7. The proximal anchor member 40a has a distal end portion 42 and a proximal end portion 44 both slidably mounted on the outer surface of the support member 51.

The system 10a also includes a pushing member 62a having a distal end with an opening having an inner diameter smaller than the inner diameter of the slidable proximal end portion 44. Distal movement of the pushing member 62a slides the proximal and distal end portions 44 and 42 against the tissue layer T2. Further distal movement of the pushing member 62a places the proximal anchor member 40a in a deployed position similar to the deployed position of the distal anchor member 30a. When both the distal and proximal anchor members 30a and 40b are deployed with the tissue layers T1 and T2 therebetween, the tissue layers T1 and T2 are fastened to one another in a manner similar to that shown in FIG. 8.

One or more retainers 58a are provided on a proximal portion of the support 51. The retainers 58a engage at least the proximal end portion 44 during sliding of the proximal end portion 44 to retain the proximal anchor member 40 in the deployed position. Preferably, the retainers 58a are locking teeth or ribs allowing for a "ratcheting" adjustment of the location of the engagement along the support 51.

During the deployment of both the distal and proximal anchor members 30a and 40a, structure, such as the pushing member 62 shown in FIGS. 1 and 2, is preferably provided to limit distal movement of the support 51. In addition, the system 10a preferably includes an introducer tube, such as the introducer tube 60 of the system 10 shown in FIGS. 1-7.

Figure 11:
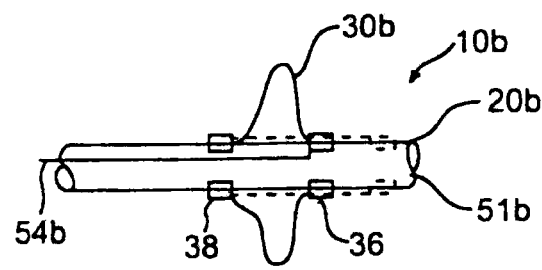
FIG. 11 is a view similar to FIG. 9 of a third embodiment of the invention.

FIG. 11 shows an embodiment of a system 10b constructed similar to the system 10a shown in FIGS. 9 and 10. The system 10b includes a distal anchor member 30b having a distal end portion 36 slidably mounted on an elongated support 51b and a proximal end portion 38 connected to the support 51b. An actuator 54b having a distal end connected to the slidable distal end portion 36 is axially movable in a lumen of the support 51b.

Distal movement of the actuator 54b moves the distal anchor member 30b from a reduced profile position, illustrated with broken lines in FIG. 11, to a deployed position, shown in FIG. 11. Preferably, the system 10b includes retainers (not shown) for retaining the distal anchor member in the deployed position. In addition, the system 10b also includes an introducer tube similar to the introducer tube 60 of the system 10 shown in FIGS. 1-7 and a proximal anchor member and pushing member similar to those of the system 10a of FIGS. 10 and 11.

Methods of treating GERD are discussed below with reference to FIGS. 1-14 Although the invention is described in connection with the structure shown in these figures, and in connection with treating GERD, it should be understood that the invention in its broadest sense is not so limited.

Figure 12:
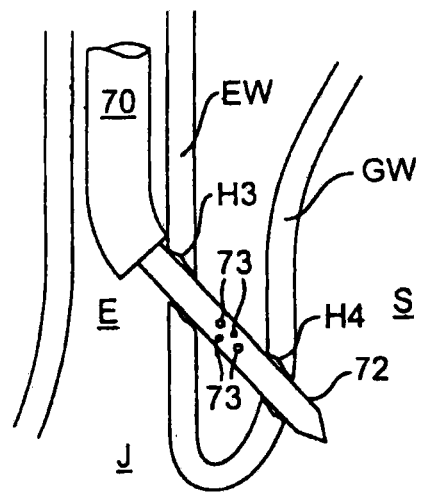
FIG. 12 is a view showing how the system initially forms a hole in the wall of the esophagus and a hole in the gastric wall during a GERD treatment procedure.

As shown in FIG. 12, an endoscope 70 is passed transorally (through the mouth of a patient) into the esophagus E until a distal end of the endoscope 70 is located adjacent to the junction J between the stomach S and the esophagus E. The endoscope 70 is preferably configured to allow a physician to visualize the wall of the esophagus EW. To view the gastric wall GW (the stomach wall), conventional radiographic or ultrasonic imaging equipment is also preferably used.

When the distal end of the endoscope 70 is properly positioned, a flexible piercing member 72, such as a needle, is introduced through the endoscope 70 and moved distally to pierce a hole H3 in the wall of the esophagus EW and a hole H4 in the gastric wall GW. During formation of the holes H3 and H4, conventional imaging equipment is preferably used to properly position the piercing member 72.

Figure 15:
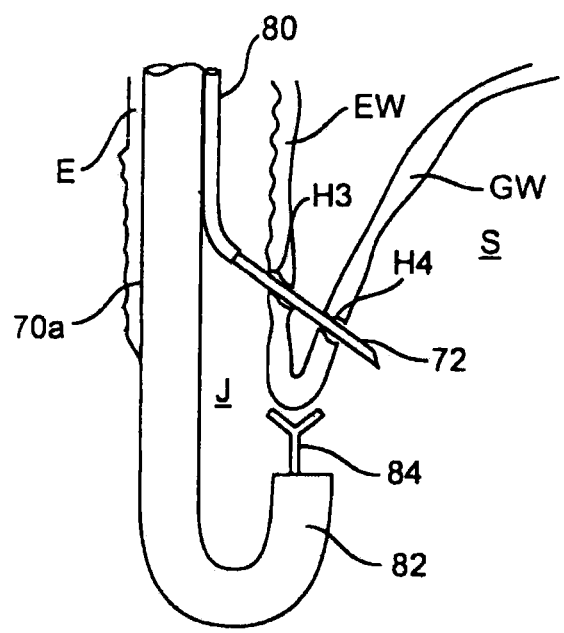
FIG. 15 is a view similar to FIG. 12 showing a tissue grasper and endoscope for use in forming the holes in the esophageal wall and gastric wall.

FIG. 15 shows an alternate embodiment of an endoscope 70a capable of being used in a GERD treatment procedure. As shown in FIG. 15, the endoscope 70a has a first channel 80 for the piercing member 72 and a second channel 82 for a tissue grasper 84 having a pair jaws. The tissue grasper 84 is preferably used to pull the gastric wall GW toward the wall of the esophagus EW to facilitate forming the holes H3 and H4 with the piercing member 72. Because the grasper 84 passes through the channel 82 of the endoscope 70, the use of the grasper 84 does not require forming a percutaneous puncture or incision in the body of the patient.

Figure 14:
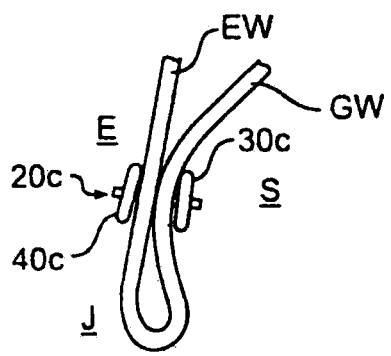
FIG. 14 is a view showing deployment of distal and proximal anchor members to secure the wall of the esophagus to the gastric wall.

As shown in FIG. 12, the piercing member 72 preferably has one or more outlets 73 positioned on a distal end portion of the piercing member 72. The outlets 73 permit dispersal of an adhesion inducing agent into the space between the esophageal wall EW and gastric wall GW by passing the agent through a lumen in the piercing member 72 and through the outlets 73. Dispersing the adhesion inducing agent between the esophageal wall EW and gastric wall GE aids in holding these walls EW and GW together when anchor members 30c and 40c of the fastener 20c are deployed as shown in FIG. 14. Any type of conventional tissue adhesive could be used for the adhesion inducing agent. For example, the tissue adhesion agent is talc slurry, gel slurry, fibrin glue, sodium morrhuate, or other bonding agent.

As those skilled in the art would recognize, the fastener 20c acts as a tissue clamp to hold the esophageal wall EW and gastric wall GE, together while the adhesion inducing agent cures or interacts with these body tissue layers to fasten them together. In an alternative embodiment, the fastener 20c is formed a materials capable of degrading in the body after the adhesion inducing agent has formed a sufficient bond between the tissue layers.

Figure 13:
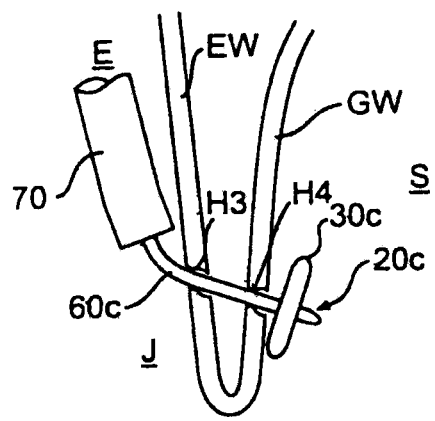
FIG. 13 is a view showing deployment of the distal anchor member in the stomach to anchor the fastener to the gastric wall.

After the piercing member 72 forms the holes H3 and H4, the piercing member 72 is removed and a fastener 20c shown in FIG. 13 is inserted transorally through the esophagus E via a lumen in the endoscope 70. Preferably, the fastener 20c is constructed like one of the fasteners 20, 20a, and 20b described above and has distal and proximal anchor members 30c and 40c shown in FIG. 14. A distal end of the fastener 20c is inserted through the holes H3 and H4 until the distal anchor member 30c is positioned in the stomach S. During the insertion of the fastener 20c through the esophagus E and the holes H3 and H4, the distal and proximal anchor members 30c and 40c are preferably in their reduced profile positions. In addition, the fastener 20c is preferably inserted while the fastener 20c is in an introducer tube 60c shown in FIG. 13. The introducer tube 60c is preferably constructed like the introducer tube 60 shown in the system of FIGS. 1-7.

In one of the preferred methods according to the invention, the piercing member 72 is not used to form the holes H3 and H4. Rather, the sharp distal end 61 of the introducer tube 60 shown in FIG. 1 is used to form the holes H3 and H4. Using the introducer 60 to form the holes H3 and H4 allows the introducer 60 to be inserted while the fastener 20c is in the introducer 60. This positions the fastener 20c in the holes H3 and H4 immediately after the holes H3 and H4 are formed. Optionally, the distal end portion of the introducer 60 includes one or more outlets (not shown) similar to the outlets 73, shown in FIG. 12, to permit dispersal of the adhesion inducing agent between the esophageal wall EW and gastric wall GW.

After a physician uses the introducer 60 or 60c to position the distal anchor member 30c in the stomach S, the distal anchor member 30c is placed in the deployed position, as shown in FIG. 13. The way in which the distal anchor member 30c is placed in the deployed position depends on the particular design of the fastener 20c. If the fastener 20c is constructed like the fastener 20 shown in FIGS. 1, 3, and 5-7, the distal anchor member 30c is placed in the deployed position by positioning the pushing member 62 shown in FIGS. 1-4, 6, and 7 against a proximal end of the fastener 20c and pulling the actuator 54 proximally. When the fastener 20c is constructed like the fastener 20a shown in FIGS. 9 and 10, the distal anchor member 30c is placed in the deployed position by moving the actuator 54a in the distal direction to slide a proximal end of the anchor member 30c toward a distal end of the anchor member 30c. If the fastener 20c is constructed like the fastener 20b shown in FIG. 11, the distal anchor member 30c is deployed by moving the actuator 54b in the proximal direction to slide a distal end of the anchor member 30c toward a proximal end of the anchor member 30c.

After the distal anchor member 30c is deployed, the fastener 20c is optionally pulled in the proximal direction to position the gastric wall GW against the wall of the esophagus EW. For example, when the fastener 70c is constructed like the fastener 20 shown in FIG. 1, the fastener 20c is pulled proximally by applying a proximal pulling force to the actuator 54 shown in FIGS. 1 and 2. Thereafter, the proximal anchor member 40c is placed in a deployed position as shown in FIG. 14. The way in which the proximal anchor member 40c is placed in the deployed position also depends on the particular design of the fastener 20c. When the fastener 20c is constructed like the fastener 20 shown in FIGS. 1, 3, and 5-7, the proximal anchor member 40c is placed in the deployed position by continued pulling of the actuator 54 in the proximal direction. When the proximal anchor member 40c is constructed like the proximal anchor member 40a shown in FIG. 10, the proximal anchor member 40c is deployed by pushing the pushing member 62a to slide proximal and distal ends of the proximal anchor member 40c toward the wall of the esophagus EW.

After the distal and proximal anchor members 30c and 40c are deployed, they are preferably retained in this deployed position. For example, the retainers 58 shown in FIGS. 5 and 7 or the retainers 58a shown in FIG. 10 are provided on the fastener 20c.

When the fastener 20c is implanted as shown in FIG. 14, components such as the endoscope 70, the introducer tube 60c, and any actuators or pushing members are removed from the patient. Preferably, additional fasteners are also implanted to secure the stomach S to the lower esophagus E at a plurality of locations. Eventually, the stomach S becomes partially wrapped on the esophagus E so that the stomach S and esophagus E are positioned similar to the way in which they would be positioned after a Nissen fundoplication procedure. As internal pressure of the stomach S increases during digestion, the stomach S applies a compressive force to the esophagus E that tends to reduce the inner luminal diameter of the esophagus E. This compressive force reduces the likelihood of the stomach contents being able to pass through the esophagus E. In other words, the lower esophagus functions like a properly functioning lower esophageal sphincter.

Figure 16:
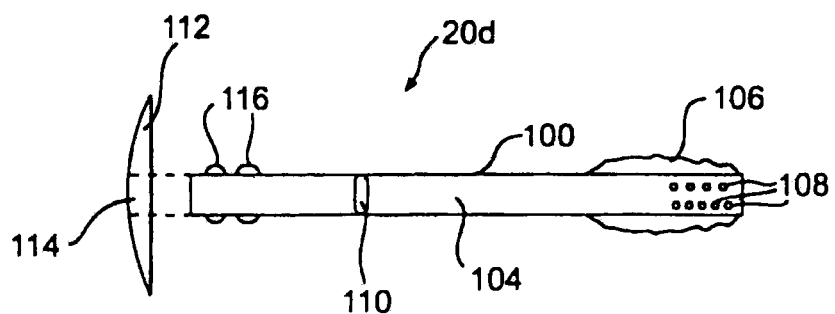
FIG. 16 is a partially exploded, side view of an embodiment of a fastener having an inflatable balloon and cap member.

FIG. 16 shows another embodiment of a fastener 20d according to the present invention. The fastener 20d includes an elongated body 100 having an internal lumen 104. An inflatable balloon 106 is mounted on the distal end portion of the body 100. The balloon 106 is formed of either an inelastic or elastic material. One or more apertures 108 on the distal end portion of the body 100 place the interior of the balloon 106 in fluid communication with the internal lumen 104.

A seal 110 in the lumen 104 prevents an inflating fluid, such as air, from escaping from the interior of the balloon 106 and from the distal end portion of the lumen 104. As explained below, the seal 110 is configured to permit the inflating fluid to enter both the distal end portion of the lumen 104 and the balloon 106 via an inflating tube 118, shown in FIG. 18, passed through the seal 110. Preferably, the seal 110 is a resilient flap of material capable of sealing inflation fluid in the distal end portion of the body 100 and in the balloon 106 when the inflating tube 118 is withdrawn from the seal 110. Alternatively, the seal 110 is a slit valve or any other type of valve capable of sealing the lumen 104 and permitting passage of the inflating tube 118 through the seal 110. In addition, the seal 110 could be a one-way valve, such as a slit valve, capable of permitting passage of the inflating fluid in only one direction in the lumen 104 without the need to pass the inflating tube 118 through the seal 110. For example, the seal could be a one-way slit valve positioned over the apertures 108.

As shown in FIG. 16, the fastener 20d further includes a cap member 112. Preferably, the cap member 112 is a low profile, disc-shaped plate having an opening 114 allowing the cap member 112 to fit slidably on the proximal end portion of the elongated body 100. Retainers 116, such as locking ribs, teeth or resilient flaps, are provided on the proximal end portion of the body 100 to retain the cap member 112 on the body 100.

Figure 17:
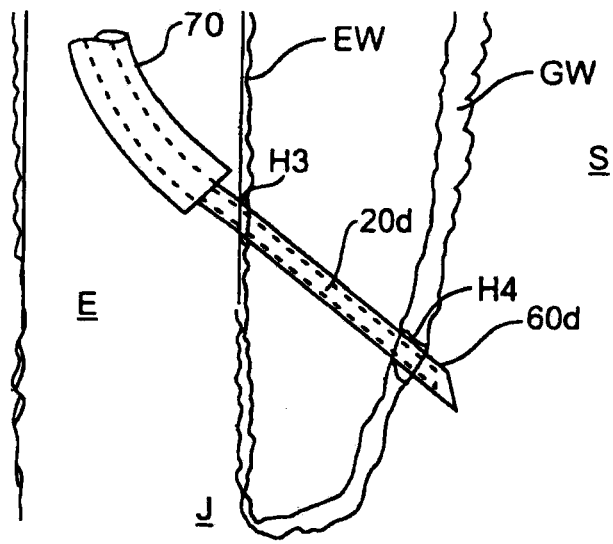
FIG. 17 is a view similar to FIG. 12 showing how holes are formed in the esophageal wall and gastric wall during use of the fastener of FIG. 16 in a GERD treatment procedure.

FIGS. 17-20 show how the fastener 20d shown in FIG. 16 is used to treat GERD. As shown in FIG. 17, an endoscope 70 is positioned in the esophagus E transorally until the distal end of the endoscope 70 is near the junction J of the esophagus E and the stomach S. Thereafter, an introducer 60d, preferably constructed like the introducer 60 shown in FIG. 1, is inserted in the endoscope 70 and through the esophageal and gastric walls EW and GW to form a hole H3 in the esophageal wall EW and a hole H4 in the gastric wall GW. Preferably, the fastener 20d is placed in a lumen of the introducer 60 when the introducer 60 forms the holes H3 and H4 so that the balloon 106 ends up in the stomach S.

Figure 18:
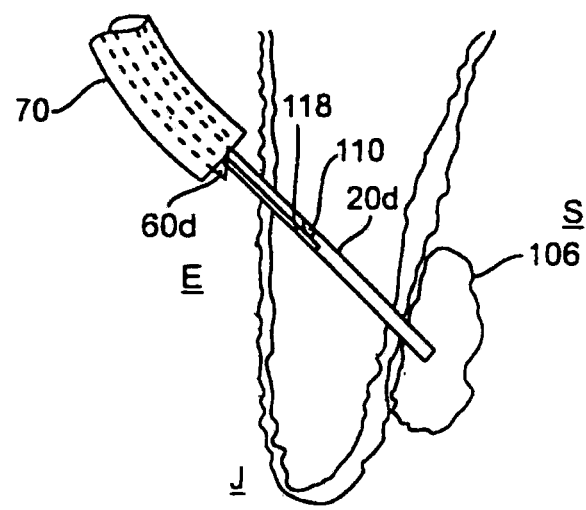
FIG. 18 shows how the balloon of FIG. 16 is inflated.

Then, the introducer 60 is retracted in the proximal direction and the balloon 106 is inflated while the balloon 106 is positioned in the stomach S, as shown in FIG. 18. To inflate the balloon 106, the inflation tube 118 is inserted in the endoscope 70 and passed through the seal 110. Fluid, such as air, flowing through the inflating tube 118 passes into the interior of the balloon 106 via the lumen 104 and apertures 108. When the balloon 106 is inflated, the balloon 106 preferably assumes a low-profile, generally disc shape in the stomach S.

Figure 19:
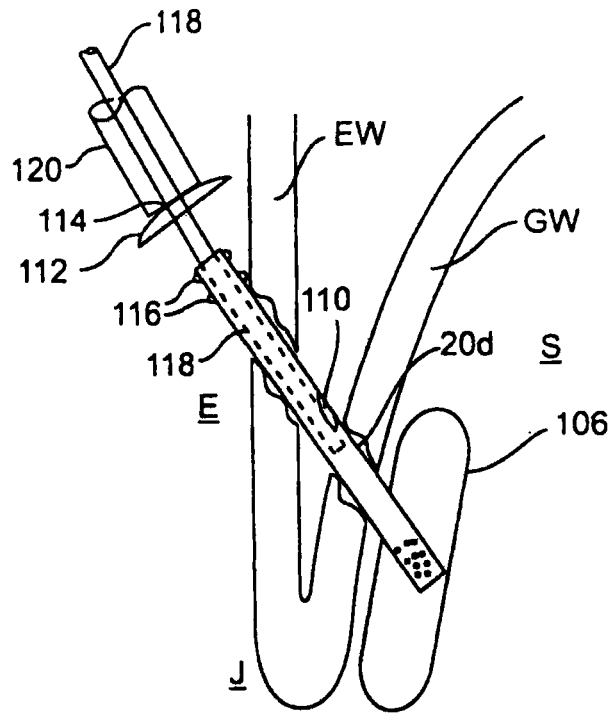
FIG. 19 shows how the cap member of FIG. 16 is pushed toward the fastener of FIG. 16.
Figure 20:
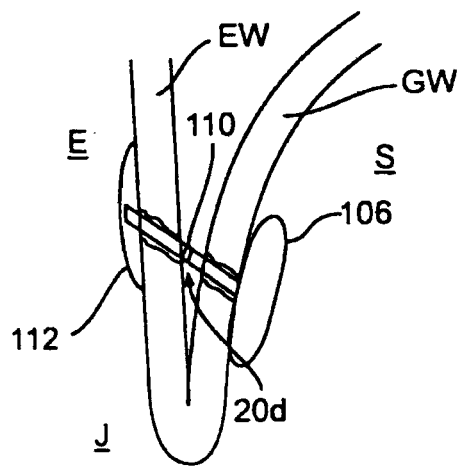
FIG. 20 is a view similar to FIG. 14 showing the fastener of FIG. 16.

While the balloon 106 is maintained in the inflated condition, the cap member 112 is advanced toward the fastener 20d, as shown in FIG. 19, by placing the inflating tube 118 in the opening 114 of the cap member 112 and pushing the cap member 112 toward the fastener 20d with pushing tube 120 having an inner lumen capable of sliding along the outer surface of the inflating tube 118. Continued pushing of the cap member 112 with the pushing tube 120 slides the cap member 112 on the body 100 and the retainers 116 retain the cap member 112 on the body 100. This sandwiches the esophageal wall EW and gastric wall GW together between the cap member 112 and inflated balloon 106, as shown in FIG. 20.

Thereafter, the inflating tube 118, pushing tube 120, and endoscope 70 are removed from the esophagus E. As the inflating tube 118 passes out of the seal 110, the seals 110 closes to trap the inflating fluid in the balloon 106 and thereby maintain the inflation of the balloon 106. As shown in FIG. 20, the fastener 20*d* fastens the gastric wall GW to the esophageal wall EW in a manner similar to the fastener 20*c* shown in FIG. 14.

Preferably, the fastener according to the invention does not extend an excess distance into the esophagus E and does not significantly interfere with normal digestion. In particular, the fastener preferably has a low profile and lacks rough or sharp edges. The portion of the fastener passing through the holes formed in the tissue preferably has a sufficient cross-sectional size to resist tearing or cutting of tissue. In addition, the fastener is preferably made of materials capable of being implanted for extended periods of time.

Preferably also, the fastener according to the invention is capable of being implanted using patient sedation without general anesthesia. If additional tissue holding force is required, multiple fasteners according the invention could be used to fasten the tissue layers together. In addition, the size of the fastener could be varied to treat pediatric or neo-natal patients. Because the fastener is relatively small even when it is used to treat adult patients, the fastener is capable of passing through the digestive tract without causing traumatic injury, if extreme esophageal gastric movements pull the fastener through the tissue layers.

Although the fastener according to the invention is preferably used to fasten the wall of the esophagus to the gastric wall in a GERD treatment procedure, the fastener could be used to fasten different layers of body tissue in different types of procedures. For example, the fastener could be used to fasten more than two layers of tissue together.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A method of treating a gastrointestinal tract, the method comprising:
    introducing an adhesion inducing agent between two opposing outer tissue surfaces of the gastrointestinal tract; and
    holding the two outer tissue surfaces of the gastrointestinal tract together while the adhesion inducing agent is between the two outer tissue surfaces;
    wherein the adhesion inducing agent is introduced before the two outer tissue surfaces are held together.

2. The method of claim 1, wherein the holding comprises using an implantable fastener to hold the two outer tissue surfaces together.

3. The method of claim 2, wherein the implantable fastener comprises a proximal anchor member and a distal anchor member, and wherein both the proximal anchor member and the distal anchor member are within the gastrointestinal tract while the implantable fastener holds the two outer tissue surfaces together.

4. The method of claim 1, further comprising piercing at least one of the two outer tissue surfaces to form a hole in the at least one of the two outer tissue surfaces.

5. The method of claim 4, further comprising inserting an introducer through the hole in the at least one of the two outer tissue surfaces for introducing the adhesion inducing agent between two outer tissue surfaces.

6. The method of claim 4, wherein holding the first outer tissue surface and the second outer tissue surface together such that the first outer tissue surface contacts the second outer tissue surface forms a fold.

7. A method of treating a gastrointestinal tract, the method comprising:
    manipulating a first outer tissue surface of the gastrointestinal tract and a second outer tissue surface of the gastrointestinal tract so that the first outer tissue surface opposes the second outer tissue surface;
    introducing an adhesion inducing agent between the first outer tissue surface and the second outer tissue surface; and
    holding the first outer tissue surface and the second outer tissue surface together while the adhesion inducing agent is between the first outer tissue surface and the second outer tissue surface;
    wherein the adhesion inducing agent fastens together the first outer tissue surface and the second outer tissue surface;
    wherein the holding comprises using an implantable fastener to hold the first outer tissue surface and the second outer tissue surface together;
    wherein the implantable fastener comprises a proximal anchor member and a distal anchor member, and wherein both the proximal anchor member and the distal anchor member are within the gastrointestinal tract while the implantable fastener holds the first outer tissue surface and the second outer tissue surface together; and
    wherein at least one of the proximal anchor member and the distal anchor member is an expandable anchor member.

8. The method of claim 7, further comprising piercing at least one of the first outer tissue surface and the second outer tissue surface to form a hole.

9. The method of claim 7, wherein the implantable fastener comprises a material that degrades in a body.

10. A method of treating a gastrointestinal tract, the method comprising:
    manipulating a first outer tissue surface of the gastrointestinal tract and a second outer tissue surface of the gastrointestinal tract so that the first outer tissue surface opposes the second outer tissue surface;
    introducing an adhesion inducing agent between the first outer tissue surface and the second outer tissue surface;
    holding the first outer tissue surface and the second outer tissue surface together such that the first outer tissue surface contacts the second outer tissue surface;
    piercing at least one of the first outer tissue surface and the second outer tissue surface to form a first hole; and
    inserting an introducer through the first hole in the at least one of the first outer tissue surface and the second outer tissue surface for introducing the adhesion inducing agent between the first outer tissue surface and the second outer tissue surface.

11. The method of claim 10, wherein the holding comprises using an implantable fastener to hold the first outer tissue surface and the second outer tissue surface together.

12. The method of claim 11, wherein the implantable fastener comprises a proximal anchor member and a distal anchor member, and wherein both the proximal anchor member and the distal anchor member are within the gastrointestinal tract while the implantable fastener holds the first outer tissue surface and the second outer tissue surface together.

13. The method of claim 10, further comprising piercing the other of at least one of the first outer tissue surface and the second outer tissue surface to form a second hole.

* * * * *